United States Patent [19]

Suto et al.

[11] Patent Number: 5,177,075
[45] Date of Patent: Jan. 5, 1993

[54] SUBSTITUTED DIHYDROISOQUINOLINONES AND RELATED COMPOUNDS AS POTENTIATORS OF THE LETHAL EFFECTS OF RADIATION AND CERTAIN CHEMOTHERAPEUTIC AGENTS; SELECTED COMPOUNDS, ANALOGS AND PROCESS

[75] Inventors: Mark J. Suto; William R. Turner; Leslie M. Werbel, all of Ann Arbor, Mich.

[73] Assignee: Warner-Lambert Company, Morris Plains, N.J.

[21] Appl. No.: 758,180

[22] Filed: Sep. 11, 1991

Related U.S. Application Data

[63] Continuation of Ser. No. 372,751, Jul. 3, 1989, abandoned, which is a continuation-in-part of Ser. No. 234,704, Aug. 19, 1988, abandoned.

[51] Int. Cl.$^5$ .......................................... C07D 217/24
[52] U.S. Cl. .................................. 514/248; 514/309; 544/237; 546/141
[58] Field of Search ................... 546/141; 544/237; 514/248, 309

[56] References Cited

U.S. PATENT DOCUMENTS

| | | | |
|---|---|---|---|
| 3,644,366 | 2/1972 | Jeanmart et al. | 546/143 |
| 3,716,542 | 2/1973 | Lenaers | 260/289 |
| 3,963,716 | 6/1976 | Inoue et al. | 544/237 |
| 4,065,456 | 12/1977 | Nakagawa | 260/289 |
| 4,282,232 | 8/1981 | Agrawal | 424/267 |
| 4,581,368 | 8/1986 | Ahmed | 514/397 |
| 4,596,817 | 6/1986 | Ahmed | 514/397 |

FOREIGN PATENT DOCUMENTS

| | | |
|---|---|---|
| 0095906 | 7/1983 | European Pat. Off. |
| 1900948 | 7/1970 | Fed. Rep. of Germany |
| 2143745 | 9/1971 | Fed. Rep. of Germany |
| WO8606628 | 11/1986 | PCT Int'l Appl. |
| 721286 | 2/1951 | United Kingdom |
| 1459559 | 10/1974 | United Kingdom |
| 1415902 | 12/1975 | United Kingdom |

OTHER PUBLICATIONS

Chaplin et al., CA 110: 185547q.
Siemann et al., CA 101: 225914e.
Vershinina, CA 147720h.
G. E. Adams, et al., Chemotherapy, vol. 7, pp. 187–206, Plenum Press, New York, 1975.
G. E. Adams, et al., Biochem & Biophysic, Res. Comm. 12:473 (1963).
J. L. Foster & R. L. Wilson (Brit. J. Radiol., 46:234 (1973))
J. Asquith, et al., Rad. Res., 60:108 (1974).
Ben Hur, et al., Rad. Res., 97:546 (1984).
T. Kato, Y. Suzumura, M. Fukushima, Anticancer Res. 1988 8,239.
Abstract Saka 24.10.73 Otsuka Pharm KK.
Abstract Saka 07.08.74 Otsuka Pharm KK.
Abstract Saka 05.02.74 Otsuka Pharm KK.
Abstract Saka 05.02.74 Otsuka Pharm KK.
Derwent Abstract No. 89–057727/08.
CA106(25)207129b.
Synthesis, 1977, p. 43 J. Org. Chem., 29:2543 (1964) Not Previously Provided.
CA106(24):205279b Khim Geterotsikl Soedi, 1984, 1, p. 132 To be provided.

*Primary Examiner*—Jane T. Fan
*Attorney, Agent, or Firm*—Joan Thierstein; Ronald A. Daignault

[57] ABSTRACT

The invention is selected, novel, and known analogs of isoquinolinones of the formula

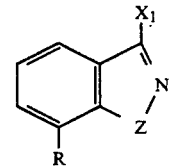

and pharmaceutically acceptable salts thereof; novel pharmaceutical compositions; and a method for enhancing the lethal effects for tumor cells to treatment having DNA damaging activity such as ionizing radiation or with chemotherapeutic agents.

8 Claims, No Drawings

SUBSTITUTED DIHYDROISOQUINOLINONES AND RELATED COMPOUNDS AS POTENTIATORS OF THE LETHAL EFFECTS OF RADIATION AND CERTAIN CHEMOTHERAPEUTIC AGENTS; SELECTED COMPOUNDS, ANALOGS AND PROCESS

CROSS-REFERENCE TO RELATED APPLICATIONS

This is a continuation of Ser. No. 07/372,751, filed Jul. 3, 1989 now abandoned which is a continuation-in-part of U.S. application Ser. No. 234,704, filed Aug. 19, 1988, now abandoned.

BACKGROUND OF THE INVENTION

The present invention relates to a method for sensitizing tumor cells to the lethal effects of DNA-damaging agents such as ionizing radiation and also some chemotherapeutic agents, using analogs of isoquinolinone and derivatives thereof. Selected novel compounds useful in the method of the invention are also the invention. More particularly, the present invention also concerns certain novel substituted dihydroisoquinolinone or thione and substituted isoquinoline-amine or -diamine compounds having utility as potentiators for the effects of radiation or certain chemotherapeutic agents.

Extensive evidence exists indicating that the radioresistance of many solid tumors is directly proportional to their hypoxic fractions. In the presence of oxygen the amount of cell kill achievable by ionizing radiation is increased. When well oxygenated cells are irradiated, irreparable lesions occur resulting from the reaction between radiation-damaged DNA and oxygen. Under hypoxic conditions such as those found in solid tumors, the initial damage that occurs from ionizing radiation is more readily repaired than that which occurs in oxic cells and ultimately leads to tumor regrowth.

The presence of hypoxic cells in tumor tissue has been demonstrated repeatedly in animal tumors, and their presence results in resistance to radiation, which makes cures with a single dose of x-rays difficult or impossible. (See G. E. Adams, et al., *Chemotherapy*, Vol. 7, pp. 187–206, Plenum Press, New York, 1975.) This problem is compounded by the fact that radiotherapy continues to be a major method for treating cancer patients. Approximately 50–60% of all cancer patients undergo some type of radiotherapy. However, the presence of these radio-resistant cells results in about 30% of these patients succumbing to a lack of control of the primary disease. Therefore, a need exists for a compound which renders solid tumors more susceptible to the lethal effects of radiation.

To overcome the problem of the resistance of hypoxic tumor cells to radiation therapy, patients have been irradiated in hyperbaric oxygen chambers. Although much experience has been gathered with this method, it is cumbersome and slow to use. Moreover, the shutdown of blood vessels is also a serious problem associated with this method.

Another solution which has been tried is the use of chemical agents which simulate the action of oxygen in their ability to sensitize hypoxic tumor cells to radiation. In 1963, Adams, et al. (*Biochem. Biophy. Res. Comm.*, 12:473 (1963)), proposed that the ability of compounds to sensitize hypoxic bacterial cells is directly related to their electron affinity. This idea has been generally verified and has aided the search for more active compounds.

In 1973, J. L. Foster and R. L. Wilson (*Brit. J. Radiol.*, 46:234 (1973)) discovered the radiosensitizing action of the antiprotozoal drug metronidazole (2-methyl-5-nitro-1H-imidazole-1-ethanol). Metronidazole is active both in vitro and in vivo as a radiosensitizer.

Another antiprotozoal drug, misonidazole (α-(methoxymethyl)-2-nitro-1H-imidazole-1-ethanol) has also recently proven to be of value as a radio-sensitizer for hypoxic tumor cells (J. Asquith, et al., *Rad. Res.*, 60:108 (1974)).

Both metronidazole and misonidazole are effective as radiosensitizers for hypoxic cells in vivo. However, both compounds exhibit serious adverse CNS side effects when administered to mice. They exhibit peripheral neuropathy effects and convulsions in mice and their CNS toxicity is thus a limiting factor for their use in humans. Nevertheless, the activity of these compounds as radiosensitizers has led to further interest and has spurred the search for additional compounds with similar activity but with diminished side effects.

Radiotherapy is now routinely given as a series of small doses of radiation (fractionated treatment) in an effort to minimize normal tissue damage and allow for tumor reoxygenation. This regimen renders the tumor more sensitive to successive radiation doses. However, substantial repair of radiation-induced damage can also occur between these small doses of radiation. This is illustrated by cell survival plots of nonexponential cell kill, which is sometimes referred to as the shoulder region of an x-ray dose response curve (i.e., cells surviving the first dose of radiation respond as unirradiated cells to the second fraction, etc.). The use of a fractionated regimen provides a small therapeutic gain with each fraction resulting in an improved gain over the course of the treatment. Inhibitors of this repair process, i.e., shoulder-modifying agents such as N-methylformamide, have been shown to sensitize tumors to the lethal effects of radiation.

Some cells when exposed to radiation do not immediately succumb to the lethal effects of radiation. This delay in toxicity, usually referred to as potentially lethal damage (PLD), accounts for some of the postirradiation toxicity that is seen when cells are treated with x-rays. PLD is DNA damage, which may be lethal if the cell attempts to replicate, but which is repaired if the cells are prevented from replicating. Compounds such as 3-aminobenzamide (PLDR inhibitors) have been shown to inhibit this postirradiation repair process, thereby sensitizing cells to the lethal effects of radiation.

Ben Hur, et al, (*Rad. Res.*, 97:546 (1984)), demonstrated that in certain cell lines the repair of damage caused by exposure to DNA-damaging agents such as ionizing radiation, was inhibited by 3-aminobenzamide. This inhibition of repair led to an enhanced killing of these cells by the damaging agents. The compounds examined are also inhibitors of poly(ADP-ribose)synthetase or adenosine diphosphate ribosyl transferase (ADPRT), an enzyme that is elevated when cells are exposed to alkylating agents and to ionizing radiation, and is through to play a role in the repair of DNA damage. Therefore, inhibitors of poly(ADP-ribose)synthetase can potentiate the lethal effects of DNA-damaging agents such as ionizing radiation and also potentiate for use in the methods of the present invention certain chemotherapeutic agents such as bleomycin, (T. Kato, Y. Suzumura, and M. Fukushima, *Anticancer Research*, 8:239 (1988)), and the like.

The present invention provides a group of compounds which enhance the lethal effects of ionizing radiation thereby making tumors more sensitive to radiation therapy. These compounds work by affecting the processes involved in the repair of radiation-induced DNA damage. Since the compounds of the invention also inhibit poly(ADP-ribose)synthetase they have utility as potentiators of certain chemotherapeutic agents as described by T. Kato, et al.

U.S. Pat. No. 4,282,232 to Agrawal discloses certain N-oxides of 2-nitro-1-ethyl-1H-imidazoles substituted with nitrogen heterocycles having utility as radiosensitizing agents. U.S. Pat. No. 4,581,368 (and its division, U.S. Pat. No. 4,596,817) disclose certain 2-nitro-1H-imidazolyl-1-[omega(1-aziridinyl)alkanols] useful as radiosensitizing agents.

Japanese Patent Application JO 1009980A (Derwent Abstract No. 89-057727/08) discloses novel 8-amino-2H-1,3-benzoxacine-2,4(3H)-dione derivatives used in radiotherapy of cancer. These compounds have a different ring system from the present invention.

European Patent Application 0 095 906 to Ahmed, et al discloses certain nitro-1H-imidazolyl-1-[omega(1-aziridinyl)alkanols] having utility as radiosensitizer agents for x-ray therapy of tumors.

Both known and novel benzamide and nicotinamide derivatives are disclosed in W086/06628 for use in sensitizing tumor cells to radiation in a similar manner as now found for the present invention. Therefore, W086/06628 is incorporated by reference.

CA106(25):207129b discloses a radiolabeled isoquinoline propanol-amine and its unchanged metabolite which is the monohydrochloride salt of a compound of the formula

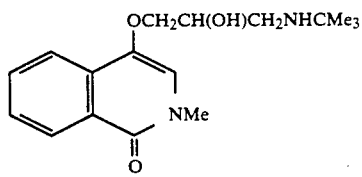

useful as an adrenergic blocker.

Isoquinolinones of the formula

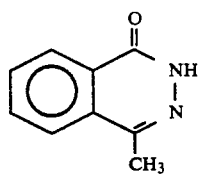

are disclosed by Yutilov et al in *Khim Geterotsikl Soedi*, 1984, 1, p. 132 without disclosure of utility. A synthesis for this compound is shown in *Synthesis*, 1977, p. 43.

The known isoquinolines of the present invention now found to be useful for sensitizing hypoxic tumor cells are disclosed as follows: Example I is purchased from Aldrich. Example II is shown by K. Nakagawa, N. Murakami, H. Hideo, and K. Tanimura, Otsuka Pharmaceutical Co., Ltd., Japan in Germ. Offen. DE 24506, May 7, 1972, 30 pp. and JP Appl. 73 120,237, Oct. 24, 1973. Example III is disclosed by K. Nakagawa and T. Nishi, Otsuka Pharmaceutical Co., Ltd., Japan in Japan Kokai JP 50/106981 [75/106981], Aug. 22, 1975, 3 pp. or Appl. or Pr. 74 15.113 5 FGb 1974 and is also a reference for Example II. Example IV is disclosed by K. Nakagawa, et al., Ohtsuka Seiyaku. K.K. Japan (Pat. Gazette Pub. No. 82-52333, Int. Cl. No. C070217/24, A61K31/47) Japanese Appl. No. 74-1511 having a filing date of Feb. 5, 1974, Early Disclosure No. 75-106976. Example VIII is shown by E. Wenkert, D. B. R. Johnston, and K. G. Dave, in *J. Org. Chem.*, 29:2534 (1964).

Isoquinolinone derivatives of the formula

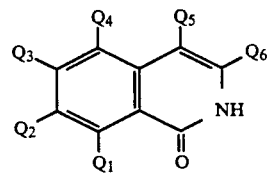

wherein $Q_1$, $Q_2$, $Q_3$, $Q_4$, $Q_5$ are H, alkyl, aralkyl, aryl, CN, $CO_2$—, —$CO_2H$, $NO_2$, $NH_2$, halo, OH, alkoxy, and acyl; and $Q_6$ is the foregoing but excluding OH are disclosed for CA106(24):205279b for use in a dry-process imaging material for photothermographic imaging. The material contains a nonphotosensitive Ag salt oxidizing agent, a reducing agent for the Ag salt, a photosensitive Ag compound of its precursor as well as the isoquinolinone derivative.

SUMMARY OF THE INVENTION

One aspect of the invention is a method of potentiating tumor cells to treatment, such as with ionizing radiation or chemotherapeutic agents in a warm-blooded animal comprising administering a compound of the formula (I)

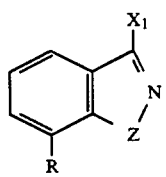

and individual isomers or mixtures thereof; or pharmacologically acceptable base and acid addition salts thereof; wherein R is $OR_1$, lower alkyl, $NR_1R_2$; halogen, trifluoromethyl,

CN, or $COX_2$ wherein $X_2$ is lower alkyl, aryl or aralkyl; and wherein $R_1$ is hydrogen, lower alkyl, benzyl, lower alkanoyl, $(CH_2)_n(CHOH)_y(CH_2)_mA$ wherein n is an integer of 1–4, y is an integer of 0 or 1, m is an integer of 0–5, and A is $OR_2$, $N(CH_3)_2$,

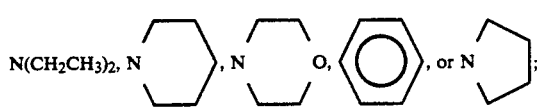

and $R_2$ is hydrogen, lower alkyl, phenyl, or benzyl;

$X_1$ is independently $OR_1$ wherein $R_1$ is as defined above, S-alkyl of from one to four carbon atoms, inclusive, or $NR_4R_5$ wherein $R_4$ and $R_5$ are independently hydrogen, lower alkyl, benzyl, lower alkanoyl, $(CH_2)_n(CHOH)_y(CH_2)_mQ$ wherein n, y, and m are as defined above and Q is $N(CH_3)_2$ or $N(CH_2CH_3)_2$;

Z is (i) —$CHR_2CHR_3$—, wherein $R_3$ is independently hydrogen, alkyl, phenyl or benzyl, (ii) $R_6C=CR_3$ or (iii) $R_2C=N$— wherein if Z is (iii) then the N of Z is attached to the ring N; and $R_2$ is independently as defined above and $R_3$ is hydrogen, lower alkyl, phenyl or benzyl, $R_6$ is hydrogen, lower alkyl, phenyl, benzyl, chlorine, bromine, or $NR_7R_8$ wherein $R_7$ and $R_8$ are independently hydrogen or lower alkyl, in unit dosage form.

Certain compounds of formula I are novel and are, therefore, also the present invention. Further, the present invention is novel pharmaceutical compositions for use as potentiators of tumor cells for treatment with ionizing radiation or chemotherapeutic agents comprising a potentiating amount of a compound of formula (II)

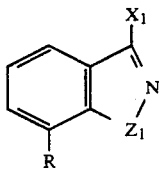

II or pharmacologically acceptable base and acid addition salts thereof wherein R is $OR_1$, lower alkyl, $NR_1R_2$; halogen, trifluoromethyl,

CN, or $COX_2$ wherein $R_1$ is hydrogen, lower alkyl, benzyl, lower alkanoyl, $(CH_2)_n(CHOH)_y(CH_2)_mA$ wherein n is an integer of 1–4, y is an integer of 0 or 1, m is an integer of 0–5, and A is $OR_2$, $N(CH_3)_2$,

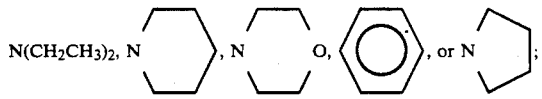

and $R_2$ is hydrogen, lower alkyl, phenyl, or benzyl;

$X_1$ is independently $OR_1$ wherein $R_1$ is as defined above, S-alkyl of from one to four carbon atoms, inclusive, or $NR_4R_5$ wherein $R_4$ and $R_5$ are independently hydrogen, lower alkyl, benzyl, lower alkanoyl, $(CH_2)_n(CHOH)_y(CH_2)_mQ$ wherein n, y, and m independently are as defined above and Q is $N(CH_3)_2$ or $N(CH_2CH_3)_2$; $X_2$ is lower alkyl, aryl, or aralkyl; and $Z_1$ is (i) $R_9C=CR_3$ wherein $R_3$ is hydrogen, alkyl, phenyl or benzyl or (ii) $R_2C=N$— wherein if $Z_1$ is (ii) then the N of $Z_1$ is attached to the ring N; and $R_2$ is independently as defined above, $R_9$ is chlorine, bromine, or $NR_7R_8$ wherein $R_7$ and $R_8$ are independently hydrogen or lower alkyl, and a pharmaceutically acceptable carrier.

The present invention is also pharmaceutical compositions for use as potentiators of tumor cells for treatment with ionizing radiation or chemotherapeutic agents comprising a potentiating amount of a compound of formula (III)

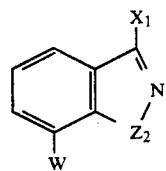

III or pharmacologically acceptable base and acid addition salts thereof wherein W is O—$(CH_2)_qA$ wherein A is $OR_2$ is as defined below, $N(CH_3)_2$, $N(CH_2CH_3)_2$,

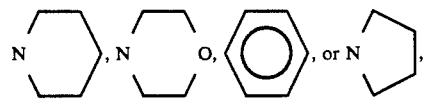

q is an integer of from one to four;

$X_1$ is independently $OR_1$ wherein $R_1$ is as defined above, S-alkyl of from one to four carbon atoms, inclusive, or $NR_4R_5$ wherein $R_4$ and $R_5$ are independently hydrogen, lower alkyl, benzyl, lower alkanoyl, $(CH_2)_n(CHOH)_y(CH_2)_mQ$ wherein n, y, and m are as defined above and Q is $N(CH_3)_2$ or $N(CH_2CH_3)_2$;

$Z_2$ is —$CHR_2CHR_3$— wherein $R_2$ and $R_3$ are independently hydrogen, alkyl, phenyl, or benzyl.

The novel compounds of formula I are:
5-amino-3,4-dihydro-1(2H)isoquinolinone, and its monohydrochloride salt;
3,4-dihydro-5-[(phenylmethyl)amino]-1(2H)isoquinolinone;
N-(1,2,3,4-tetrahydro-1-oxo-5-isoquinolinyl)acetamide;
3,4-dihydro-5-methyl-1(2H)isoquinolinone;
5-ethyl-3,4-dihydro-1(2H)-isoquinolinone;
5-chloro-3,4-dihydro-1(2H)isoquinolinone;
3,4-dihydro-5-methoxy-1-(methylthio)isoquinoline;
3,4-dihydro-3,5-dimethyl-1(2H)isoquinolinone;
3,4-dihydro-5-methyl-1-(methylthio)isoquinoline;
3,4-dihydro-5-(dimethylamino)-1(2H)isoquinoline and its hydrochloride salt;
5-methoxy-4-methyl-1(2H)-phthalazinone;
3,4-dihydro-5-[3-(1-piperidinyl)propoxy]1(2H)-isoquinolinone;
3,4-dihydro-5-[2-(1-piperidinyl)ethoxy](1(2H)-isoquinolinone;
3,4-dihydro-5[4-(1-piperidinyl)butoxy]1(2H)-isoquinolinone;
5-ethoxy-3,4-dihydro-1(2H)-isoquinolinone;
3,4-dihydro-5-propoxy-1(2H)-isoquinolinone;
5-butoxy-3,4-dihydro-1(2H)-isoquinolinone;
3,4-dihydro-5-(2-hydroxy-3-methoxypropxy)1(2H)-isoquinolinone;
3,4-dihydro-5-(2-hydroxy-3-phenoxypropoxy)1(2H)-isoquinolinone;
3,4-dihydro-5-(2-hydroxy-3-phenylpropoxy)1(2H)-isoquinolinone; or
3,4-dihydro-5-(phenylethoxy)-1(2H)-isoquinolinone.

The compounds of formula II that are novel and therefore are also the present invention are:
4-bromo-5-methyl-1(2H)-isoquinolinone;
4-bromo-5-hydroxy-1(2H)-isoquinolinone.

Therefore, in another aspect the invention is directed to the selected compounds of formula I, II and III that are novel and the manufacture for use as potentiating tumor cells to the treatment with ionizing radiation or chemotherapy as well as compounds of formula II and III in pharmaceutical compositions therefor.

DETAILED DESCRIPTION OF THE INVENTION

In the compounds of formula I the term "lower alkyl" is meant to include a straight or branched alkyl group having one to six carbon atoms such as, for example, methyl, ethyl, propyl, butyl, pentyl or hexyl and isomers thereof.

"Alkyl of from one to four carbon atoms, inclusive," is meant methyl, ethyl, propyl, butyl and isomers thereof.

Halogen includes particularly fluorine, chlorine or bromine.

Lower alkanoyl is a

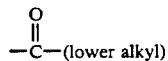

group having lower alkyl as defined above.

Aryl is phenyl unsubstituted or substituted by one or two substituents selected from the group consisting of halogen, hydroxy, alkoxy, alkylthio, amino including morpholino, acyloxy, and acylamido and their thio analogs, lower alkylsulfonyl or lower alkylphosphonyl, carboxy, lower alkoxycarbonyl, or carbamyl or lower alkylcarbamyl.

Aralkyl is an aryl attached through an alkylenyl of from one to four carbon atoms, inclusive.

Appropriate compounds of formula I are useful in the free base form, in the form of base salts where possible, and in the form of acid addition salts. The three forms are within the scope of the invention. In practice, use of the salt form amounts to use of the base form. Pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di-, and triethanolamine; amino acids such as arginine and lysine; guanidine; N-methylglucosamine; N-methylglucamine; L-glutamine; N-methylpiperazine; morpholine; ethylenediamine; N-benzylphenethylamine; trihydroxymethyl)aminomethane; and the like. (See for example, "Pharmaceutical Salts," J. Pharm. Sci., 66(1):1-19 (1977).)

The acid addition salts of said basic compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The compounds of the invention may contain an asymmetric carbon atom. Thus, where possible, the invention includes the individual stereoisomers, and mixtures thereof. The individual isomers may be prepared or isolated by methods known in the art.

Preferred compounds useful in sensitizing tumor cells as described herein are of the formula I as defined above.

Likewise, preferred compounds useful in sensitizing tumor cells as described herein are of the formula II as defined herein. Also the present invention is for preferred compounds as found in the Examples of the following specification.

The more preferred compounds of the methods and pharmaceutical compositions are those wherein $X_1$ is OH.

The most preferred compound useful in radiosensitizing hypoxic tumor cells as described herein is:

3,4-dihydro-5-methyl-1(2H) isoquinolinone.

Of the compounds defined as formula II in the compositions of the present invention the most preferred are 4-bromo-5-methyl-1(2H)-isoquinolinone and 4-bromo-5-hydroxy-1(2H)-isoquinolinone.

Certain of the compounds of formula I are known and thus available. The novel compounds as noted above can be prepared by known methods from starting materials that are known and available commercially or can be prepared by known methods in the literature.

It is understood that tautomeric forms, when possible, of the compounds of formula I are included in the invention. For example, note the following compounds:

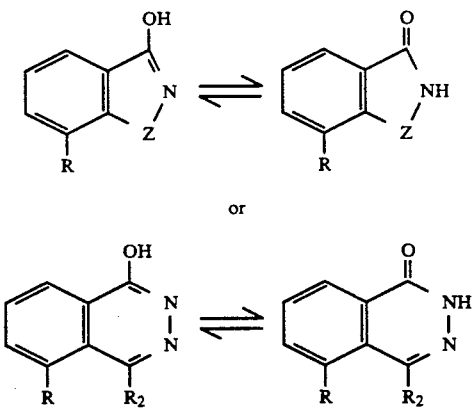

The formulation and administration of the compounds of formula I for use to sensitize tumor cells in warm-blooded animal hosts will typically be used in radiotherapy of human patients, however, the compounds of formula I may also be used to sensitize tumor cells in other warm-blooded animal species.

Although the present invention is not meant to be limited to hypoxic tumors its utility is to include such tumors. Hypoxia is believed to be associated with all types of solid malignant neoplasms. The compounds of the invention may, therefore, by used to radiosensitive neoplastic epithelial cells, endothelial cells, connective tissue cells, bone cells, muscle cells, nerve cells, and brain cells. Examples of carcinomas and sarcomas that may be radiosensitized include carcinomas such as epithelial cells, alveolar cell, basal cell, basal squamous cell, cervical, renal, liver, Hurthle, Lucke, mucinous and Walker, and sarcomas such as Abernathy's, alveolar soft part, angiolithic, botyroid, encephaloid, endometria stroma, Ewing's fascicular, giant cell, lymphatic, Jensen's, justocortical osteogenic, Kaposi's, medullary, and synovial. Specific examples of tumors that have been radiosensitized with other radiosensitizers are reported in Adams, G. E., *Cancer: A Comprehensive Treatise* (F. Becker, ed), Vol. 6, pp. 181-223, Plenum, New York, 1977.

The compounds of formula I of the present invention may be administered to patients orally or parenterally (intravenously, subcutaneously, intramuscularly, intraspinally, intraperitoneally, and the like). It is likely, however, that the preferred route for human administration will be intravenous. When administered parenterally they will normally be formulated in a unit dosage injectable form (solution, suspension, emulsion) with a pharmaceutically acceptable vehicle. Such vehicles are typically nontoxic and nontherapeutic. Examples of such vehicles are water, aqueous vehicles such as saline, Ringer's solution, dextrose solution, and Hanks' solution and nonaqueous vehicles such as fixed oils (such as corn, cottonseed, peanut, and sesame), ethyl oleate, and isopropyl myristate. Sterile saline is a preferred vehicle and the compounds are sufficiently water soluble to be made up as a solution for all foreseeable needs. The vehicle may contain minor amounts of additives such as substances that enhance solubility, isotonicity, and chemical stability, e.g., antioxidants, buffers, and preservatives. When administered orally (or rectally) the compounds will usually be formulated into a unit dosage form such as a tablet, capsule, suppository or cachet. Such formulations typically include a solid, semi-solid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, aginates, tragacanth, gelatin, syrup, methylcellulose, polyoxyethylene sorbitan monolaurate, methyl hydroxybenzoate, propyl hydroxybenzoate, talc, and magnesium stearate.

The amount of compound administered to the subject is sufficient to radiosensitize the malignant neoplasm to be treated but below that which may elicit toxic effects. This amount will depend upon the type of tumor, the species of the subject being treated, the indication dosage intended, and the weight or body surface of the subject which can be determined by a physician of skill in the art. The radiation may be administered to humans in a variety of different fractionation regimens, i.e., the total radiation dose is given in portions over a period of several days to several weeks. These are most likely to vary from daily (i.e., five times per week) doses for up to six weeks, to once-weekly doses for four to six weeks. An individual dose of the compounds of formula I of the present invention is given before each radiation treatment and is likely to be in the range of 0.01 to 20 mmol/kg and usually in the range of 0.1 to 2 mmol/kg.

Since radiosensitivity is directly related to the concentration of the administered compound in the tumor, the compounds will ideally be administered at a time such that their peak concentration in the hypoxic cells occurs at a predictable time in relation to the time the tumor is exposed to radiation. This time will depend upon the manner in which the compound is administered, the particular dosage form employed, the type of tumor, and the species of the patient. Intravenous administration will typically be done about ½ to 1 hour prior to radiation exposure to provide maximum radiosensitization. Oral administration may require a somewhat longer lag because the compound must first pass through the gastrointestinal barrier.

EXAMPLES

The following examples further illustrate the compounds of the invention and methods for synthesizing them and using them. These examples are not intended to limit the invention in any manner.

EXAMPLE I 1,5-Dihydroxyisoquinoline

Commercially available. Recrystallized from ethanol; mp 279°-281°.

EXAMPLE II 3,4-Dihydro-5-hydroxy-1(2H)-isoquinolinone

A mixture of 10.0 g (62.0 mmol) of 1,5-dihydroxyisoquinoline in 500 ml of HOAc and 2 g of 20% Pd-C was hydrogenated at room temperature until the required amount of hydrogen was absorbed. The solution was filtered and concentrated. The resulting solid was recrystallized from water (200 ml) to give 8.74 g (86%) of product; mp 195°-198°.

EXAMPLE III 3,4-Dihydro-5-(2-oxiranylmethoxy)-1(2H)-isoquinolinone

To a solution of sodium methoxide (made from 2.4 g (106 mmol) of sodium) in 360 ml of methanol was added 14.5 g (106 mmol) of 3,4-dihydro-5-hydroxy-1(2H)-isoquinolinone. Then 22.2 g of epichlorohydrin in 250 ml of methanol was added dropwise at 55°. After 18 hours an additional 5 g of epichlorohydrin was added and the mixture was stirred for two hours more. The reaction was cooled and concentrated. The residue was chromatographed ($SiO_2$, chloroform/methanol 8:1) to provide 7.9 g (34%) of the desired product. An analytical sample was obtained by recrystallization from chloroform; mp 165°-166°.

EXAMPLE IV 3,4-Dihydro-5-[2-hydroxy-3-(1-piperidinyl)propoxy]-1(2H)-isoquinolinone A mixture of 3.0 g (13.7 mmol) of 3,4-Dihydro-5-(2-oxiranylmethoxy)-1(2H)-isoquinolinone, 1.4 g of piperidine (13.7 mmol), and 30 ml of ethanol was heated at reflux for five hours. The mixture was concentrated and the residue was recrystallized from ethanol/acetone (2/3) to give 2.78 g (67%) of the desired product; mp 162°-164°.

EXAMPLE V 3,4-Dihydro-5-methoxy-1(2H)-isoquinolinone

To a refluxing solution of 5.5 g (33.7 mmol) of 3,4-dihydro-5-hydroxy-1(2H)-isoquinolinone in 35 ml of 2N NaOH and 70 ml of methanol was added 4 ml of dimethyl sulfate. At two-hour intervals additional amounts of NaOH and dimethyl sulfate were added and the reaction was heated under reflux conditions overnight. The mixture was concentrated, diluted with 300 ml of water, and acidified (pH 2-3) with concentrated sulfuric acid. The solid which formed was collected and dried to give 5.3 g (89%) of material sufficiently pure for the next step. An analytical sample was obtained by recrystallization from acetone; mp 147°-149°.

EXAMPLE VI 5-(Acetyloxy)-3,4-dihydro-1(2H)-isoquinolinone

A mixture of 2.0 g (12.3 mmol) of 3,4-dihydro-5-hydroxy-1(2H)-isoquinolinone, 2.0 g (52 mmol) of $K_2CO_3$ and 0.75 g of acetic anhydride in 20 ml of DMF was stirred at room temperature for 2.5 days. The mixture was then warmed to 70°-80° and an additional 1.5 g of acetic anhydride was added and stirring was continued for five hours. The reaction was poured into 250 ml of water and the resulting solid was collected, washed with water, and air dried. It was recrystallized from EtOH and then chromatographed ($SiO_2$, 9:1 methylene chloride/MeOH) to give 0.72 g (29%) of product; mp 189°-193°.

EXAMPLE VII 3,4-Dihydro-5-(phenylmethoxy)-1(2H)-isoquinolinone

To a mixture of 2.4 g (14.7 mmol) of 3,4-dihydro-5-hydroxy-1(2H)-isoquinolinone and 2.5 g of cesium carbonate in 30 ml of ethanol was added 2.5 g (15.0 mmol) of benzyl bromide. The mixture was stirred for 18 hours at room temperature. Then an additional 2.5 g of cesium carbonate and 2.5 g of benzyl bromide was added and the mixture was heated under reflux conditions for four hours. The reaction was partitioned between water and ether, the ether layer was filtered (to remove solid), dried ($MgSO_4$), and concentrated. The residue was dissolved in hexane, filtered, concentrated, and the residue was crystallized from ethanol to give 3.01 g (81%) of the desired product; mp 171°-173°.

EXAMPLE VIII

5-Amino-1(2H)-isoquinolinone

A mixture of 4.0 g (21 mmol) of 5-nitroisoquinolinone in 100 ml HOAc and 0.5 g 5% Pd-C was hydrogenated at room temperature for 18 hours (three atmospheres). The mixture was filtered and concentrated to give a solid. The solid was dissolved in ethanol (50 ml) and 10 ml of saturated ethanolic HCl was added. The solution was cooled and the resulting solid was collected. It was dissolved in water and the solution was neutralized with 100 ml concentrated $NH_4OH$. The precipitate was collected, dissolved in 150 ml of hot methanol, treated with charcoal, filtered, and diluted with water. Upon cooling, 1.10 g (32%) of the desired product was collected; mp 258°-259°.

EXAMPLE IX

5-Amino-3,4-dihydro-1(2H)-isoquinolinone, monohydrochloride

A mixture of 19.0 g (119 mmol) of 5-nitroisoquinolinone in 1.7 liters of ethanol and 1.0 g of 5% Pd-C was hydrogenated at room temperature for 2.1 hours (three atmospheres). Then 4.0 g of 20% Pd-C was added and hydrogenation was continued. After 19.8 hours an additional 2.0 g of 20% Pd-C was added. At the end of 40 hours the reaction was filtered and concentrated. The residue was recrystallized from ethanol/hexane to give 13.4 g (70%) of product suitable for further reaction.

An analytical sample was obtained by dissolving a sample in ethanol, followed by treatment with a saturated solution of ethanol/HCl, cooling and collecting the resulting hydrochloride salt; mp 284°-302°.

EXAMPLE X 3,4-Dihydro-5-[(phenylmethyl)amino]-1(2H)-isoquinolinone

To a solution of 2.0 g (12.3 mmol) of 5-amino-3,4-dihydro-1(2H)-isoquinolinone, monohydrochloride in 10 ml of THF was added 2.6 g (14.76 mmol) of benzylbromide and 2 ml of triethylamine. The mixture was heated under reflux for six hours and then poured into ice water and extracted with ether. The ether extracts were washed with water, dried ($MgSO_4$), and concentrated. The residue was chromatographed ($SiO_2$, ether to 10:1 ether/methanol) to provide 0.6 g of the dibenzylated product and 0.95 g (31%) of the desired monobenzylated product after crystallization from ethanol; mp. 142°-144°.

EXAMPLE XI

N-(1,2,3,4-Tetrahydro-1-oxo-5-isoquinolinyl)acetamide

To 1.0 g (6.17 mmol) of 5-amino-3,4-dihydro-1(2H)-isoquinolinone was added 3 ml of acetic anhydride and the solution was warmed on a steam bath for one hour. It was poured into ice water and heated on a steam bath until all material dissolved. The solution was allowed to cool, the solid was collected, washed with water, and dried to give 0.7 g (56%) of product; mp 244°-246°.

EXAMPLE XII 3,4-Dihydro-5-methyl-1(2H)-isoquinolinone

Trans-2-methyl-cinnamic acid

See H. Zimmer, D. C. Armbruster, and L. J. Trauth, *J. Heterocyclic Chem.*, 3:232 (1966).

A mixture of 35.1 g (0.29 mol) of o-tolualdehyde, 47.6 g (0.46 mol) of acetic anhydride, and 18 g (0.174 mol) of fused and pulverized potassium acetate was heated at 155°-160° for 15 minutes and then at 165°-170° for 12 hours. The mixture was diluted with 1 liter of ice water and steam distilled to remove excess aldehyde. On cooling, a yellow solid formed. The solid was collected, washed with water, dissolved in chloroform, treated with charcoal, and filtered. The filtrate was concentrated and the residue was recrystallized from ethanol/ether to give 16.5 g (35%) of trans-2-methyl-cinnamic acid; mp 173°-175°.

Methyl-benzenepropanoic acid

See W. E. Backmann and E. K. Raunio, *J. Amer. Chem. Soc.*, 72:2530 (1950).

A mixture of 14.5 g (8.95 mmol) of trans-2-methylcinnamic acid in 200 ml of THF and 1.0 g 5% Pd-C was hydrogenated at room temperature (three atmospheres). The mixture was filtered and the pale yellow filtrate was evaporated to give 14.5 g of a tan solid suitable for use in the next step. An analytical sample was obtained by recrystallization from n-hexane; mp 101°-103°.

2,3-Dihydro-4-methyl-1H-inden-1-one

See K. T. Potts and R. Robinson, *J. Chem. Soc.*, 2466 (1955).

A solution of 12.0 g (73.2 mmol) of 2-methylbenzenepropanoic acid in 125 ml of methylene chloride was added portion-wise to 500 g of polyphosphoric acid. The mixture was heated for six hours on the steam bath and the resulting orange solution was diluted with 1.5 l of ice. The solid was collected, washed with water, and air dried to give 7.2 g crude material. Recrystallization from ethanol/water gave 5.8 g of the desired product; mp 94°-97°. Extraction of the original diluted reaction mixture with methylene chloride gave an additional lot. Total recovery was 7.7 g (72%).

3,4-Dihydro-5-methyl-1(2H)-isoquinolinone

A mixture of 4.7 g (32.2 mmol) of 2,3-dihydro-4-methyl-1H-inden-1-one and 53 g of trichloroacetic acid was heated to 65°. To the resulting solution was added 4.2 g (64.4 mmol) of sodium azide and the mixture was kept at 65° for 18 hours. An additional 1.0 g of sodium azide was then added and heating continued for another four hours. The mixture was diluted with 200 ml of ice water and extracted with ether. The ether extracts were washed with water, saturated sodium hydrogen carbonate, dried (MgSO4), and concentrated. The residue was chromatographed (SiO2, ether to ether/methanol 95/5). The resulting product was recrystallized from toluene to give 2.45 g (47%) of product; mp 141°-143°.

EXAMPLE XIII

5-[Dimethylamino)methoxy]-3,4-dihydro-1(2H)-isoquinolinone

To 7.5 g of 37% formaldehyde (85 mmol) was added 10 ml of cold acetic acid followed by 7.5 g (85 mmol) of 40% aqueous dimethylamine. To this solution was added 3.0 g (17.0 mmol) of 3,4-dihydro-5-hydroxy-1(2H)-isoquinolinone. The mixture was kept at room temperature for one hour and then heated at 40° for 18 hours. The cooled mixture was poured into 500 ml of saturated sodium hydrogen carbonate and the resulting solid was collected and recrystallized from ethanol to give 0.95 g (25%) of product; mp 151°-154°.

EXAMPLE XIV

5-Methoxy-1(2H)-isoquinolinone

To 3.0 g (18.6 mmol) of 1,5-dihydroxyisoquinoline in 80 ml methanol and 20 ml of water was added 0.78 g of 50% sodium hydroxide (39 mmol) and 2 ml of dimethyl sulfate. The mixture was heated under reflux for two hours. An additional 4.0 ml of dimethyl sulfate and 10 ml of 50% sodium hydroxide was then added and refluxing continued for an additional hour. The mixture was diluted with 200 ml of water and concentrated to half the original volume. The resulting solid was collected and washed with water. Recrystallization from ethanol gave 2.1 g (64%) of the desired product; mp 215°-217°.

EXAMPLE XV

5-Ethyl-3,4-dihydro-1(2H)-isoquinolinone

2-Ethylphenylmethyl propanedioic acid, diethyl ester

A mixture of 19.7 g (131 mmol) of 2-ethylbenzoic acid and 100 ml of thionyl chloride was heated under reflux for five hours. The reaction was concentrated, 50 ml of toluene was added, and the mixture was concentrated again to remove the last traces of thionyl chloride (done three times). The resulting dark liquid was dissolved in 50 ml of DMF and added dropwise over 20 minutes at 0° to a solution of sodium diethyl malonate in 250 ml of DMF [prepared by adding 23.0 g (143 mmol) of diethyl malonate in 100 ml of DMF to a suspension of 5.8 g (145 mmol) of NaH (60% oil dispersion) which had been washed with n-hexane and suspended in 150 ml of DMF]. The mixture was allowed to warm to room temperature over two hours and then was poured into 500 ml of ice water and extracted with ether. The ether extracts were washed with saturated sodium chloride, dried (MgSO4), and concentrated. The residue was chromatographed (SiO2, n-hexane to 9:1 n-hexane/ether) to give 16.5 g (45%) of a colorless oil suitable for use in the next step.

A mixture of 13.4 g (45.9 mmol) of the ketone in 100 ml of ethanol and 2.0 g of 20% Pd-C was hydrogenated at room temperature until two equivalents of hydrogen were taken up. The mixture was filtered and concentrated. The residue was chromatographed (SiO2, hexane to 9:1 hexane/ether) to give 3.5 g (27%) of 2-ethylphenylmethyl propanedioic acid, diethyl ester as a colorless oil.

2-Ethylbenzenepropanoic acid

A mixture of 2.2 g (7.9 mmol) of 2-ethylphenylmethyl propanedioic acid, diethyl ester and 100 ml of 6N HCl was heated under reflux for 18 hours. The mixture was cooled and filtered to give 1.1 g of solid. Recrystallization from toluene/n-hexane gave 2-ethylbenzenepropanoic acid; mp 87°-91°.

2,3-Dihydro-4-ethyl-1H-inden-1-one

A mixture of 1.5 g (8.4 mmol) of 2-ethylbenzenepropanoic acid and 20 ml of polyphosphoric acid was heated at 85°-90° for three hours. The orange solution was added to 300 ml of ice water and stirred for one hour. The solid was collected to give 1.1 g of material suitable for the next step. An analytical sample was obtained by recrystallization from toluene/n-hexane; mp 64°-66°.

5-Ethyl-3,4-dihydro-1(2H)-isoquinolinone

A mixture of 0.9 g (5.63 mmol) of 2,3-dihydro-4-ethyl-1H-inden-1-one and 20 g of trichloroacetic acid was heated at 60°-65° for 30 minutes. To this was added 2.5 g (38.3 mmol) of sodium azide and the mixture was heated at 60°-65°, under nitrogen, for 18 hours. It was poured into 200 ml of ice water and extracted with methylene chloride. The organic layer was washed with saturated sodium hydrogen carbonate, saturated sodium chloride, dried (MgSO4), and concentrated. The residue was chromatographed (SiO2) using a gradient from pure methylene chloride to 19:1 methylene chloride-methanol to give a solid which was rechromatographed using 98:1 methylene chloride-methanol. Recrystallization from toluene/hexane gave 0.21 g (21%) of product; mp 123°-126°.

EXAMPLE XVI

5-Chloro-3,4-dihydro-1(2H)-isoquinolinone 3-(2-Chlorophenyl)-propanoic acid

A solution of 25.0 g of 3'-chlorocinnamic acid (137 mmol) was hydrogenated in 200 ml of THF with 2 g of Ra/Ni at three atmospheres for 16 hours. Then an additional 1.5 g of Ra/Ni was added and the reaction continued for an additional two hours. The solution was filtered and concentrated to give 23.2 g (92%) of material suitable for the next step. A 3.0-g sample was recrystallized from toluene to give 1.6 g of analytical material (53% recovery); mp 97°–99°.

A mixture of 200 ml of polyphosphoric acid and 23.6 g (128 mmol) of 3-(2-chlorophenyl)-propanoic acid was heated on the steam bath for six hours. The mixture was allowed to cool, diluted with 500 ml of water, and the resulting solid collected. The solid was partitioned between ether and saturated sodium bicarbonate, the ether layer was separated, dried (MgSO$_4$), and concentrated to a solid. The solid was crystallized from ether/hexane to give 7.8 g (37%) of 4-chloro-2,3-dihydro-1H-inden-1-one; mp 89°–92°.

5-Chloro-3,4-dihydro-1(2H)-isoquinolinone

To 100 g of trichloroacetic acid preheated to 65° was added 7.5 g (45.0 mmol) of 4-chloro-2,3-dihydro-1H-inden-1-one. The mixture was stirred for 0.5 hours and then 4.0 g (62 mmol) of sodium azide was added. Heating was continued for 18 hours then 500 ml of ice water was added and the mixture was extracted with ether. The ether extracts were washed with water, saturated K$_2$CO$_3$, dried (MgSO$_4$), and concentrated to give 5.8 g of a solid which was a mixture of the desired product and the quinoline analog. The solid was chromatographed (SiO$_2$, ether) and the fractions with the slower Rf material were concentrated and the residue was recrystallized from ethanol to give 2.00 g (25%) of the desired product; mp 143°–148°.

EXAMPLE XVII 3,4-Dihydro-5-methoxy-1-(methylthio)-isoquinoline 3,4-Dihydro-5-methoxy-1(2H)-isoquinolinethione A mixture of 1.0 g (5.6 mmol) of 3,4-dihydro-5-methoxy-1(2H)-isoquinolinone and 1.3 g (5.9 mmol) of phosphorous pentasulfide in 50 ml of xylenes was heated under reflux for one hour. The supernatant was decanted from the yellow residue and the residue was washed with xylenes. The xylenes were concentrated to give a yellow semisolid which was crystallized from ethanol to provide 0.62 g (57%). This material was recrystallized from methylene chloride/n-hexane to give 0.60 g of analytical material (56%); mp 168°–170°.

To 0.42 g of 60% sodium hydride oil dispersion in 20 ml of THF was added 2.01 g (10.4 mmol) of 3,4-dihydro-5-methoxy-1(2H)-isoquinoline thione at 0°. Then a solution of 1.5 g (10.4 mmol) of methyl iodide in 20 ml of THF was added and the mixture was allowed to warm to room temperature during three hours. The reaction was partitioned between water and ether. The ether layer was dried (MgSO$_4$), filtered through a bed of silica gel, and concentrated to an oil (1.34 g, 62%). The oil was dissolved in 5 ml of ethanol and water was added until cloudy. Slow evaporation of the solution gave 0.82 g (38%) of product; mp 44°–46°.

EXAMPLE XVIII 3,4-Dihydro-3,5-dimethyl-1(2H)-isoquinolinone 2,4-Dimethylindanone was prepared in a manner similar to that used in the preparation of the 4-methylindanone, substituting methyldiethyl malonate for diethylmalonate. The desired indanone was prepared in 37% yield; mp 89°–92°.

To 100 g of trichloroacetic acid preheated to 65° was added 9.3 g (62.8 mmol) of 2,4-dimethylindanone. After stirring for 0.5 hours, 6.1 g (94.2 mmol) of sodium azide was added and heating continued for an additional 18 hours. By tlc, further heating appeared to lead to more decomposition than product formation. The reaction was poured into 500 ml of ice water and extracted with methylene chloride. The extracts were washed with water, saturated NaHCO$_3$, dried (MgSO$_4$), and concentrated to give a dark oil. The oil was chromatographed (SiO$_2$, 7:1 ether/n-hexane). Fractions from the major faster Rf product were concentrated to give a solid which was recrystallized from nitromethane to give 0.54 g (5%) of the undesired quinoline. Fractions from the minor slower Rf product were evaporated to give a solid which was recrystallized from ethyl acetate providing 0.32 g (3%) of the desired product; mp 154°–156°.

EXAMPLE XIX 3,4-Dihydro-5-methyl-1-(methylthio)-isoquinoline 3,4-Dihydro-5-methyl-1(2H)-isoquinolinethione To a solution of 2.9 g (18 mmol) of 3,4-dihydro-5-methyl-1(2H)-isoquinolinone in 30 ml of pyridine was added 4.0 g (18 mmol) of P$_2$S$_5$. The mixture was heated at 90° for two hours, poured into 500 ml of water, and heated on a steam bath for two hours. The mixture was cooled and the solid collected. The solid was dissolved in 70 ml of methylene chloride and filtered through a pad of silica gel. The solid obtained after concentration was recrystallized from 15 ml of toluene to give 1.1 g of yellow plates. An additional 1.4 g was obtained by extracting the aqueous work-up with ether to give a total yield of 2.5 g (78%); mp 181°–183°.

To 0.15 g of 60% sodium hydride (3.70 mmol) which was washed with n-hexane and suspended in 15 ml of THF was added dropwise at 0 a solution of 0.50 g (2.82 mmol) of 3,4-dihydro-5,6-dihydroxy-1(2H)-isoquinolinethione in 5 ml of THF. The thick white suspension which formed was stirred for 0.5 hours at 0°–5° and then 0.45 g (2.82 mmol) of methyl iodide in 5 ml THF was added and stirring continued for one hour. The resulting yellow solution was diluted with ether, washed with saturated NaCl, dried (Na$_2$SO$_4$), and concentrated. The resulting oil was recrystallized from 1 ml of n-hexane to give pale yellow crystals, 0.55 g (100%); mp 43°–45°.

EXAMPLE XX

5-Methoxy-3-phenyl-1(2H)-isoquinolinone

To a solution of 4.53 mmol of LDA at −78° (generated by adding a 3 ml of 1.55M n-butyllithium in n-hexane to 0.33 g of diethylamine in 5 ml of THF) was added 1.0 g (4.52 mmol) of N,N-diethyl-3-methoxy-2-methyl-benzamide in 10 ml THF. Then a solution of 4.53 mmol of trimethylsilyl benzylamine [generated from 0.81 (4.53 mmol) of hexamethyldisilazane in 2 ml of n-hexane added to 3 ml of 1.55N n-butyllithium followed by the addition of 0.48 g (4.53 mmol) of benzaldehyde in 2 ml of n-hexane] was added and stirring continued at −78° for two hours and then at room temperature for one hour. The reaction was cooled to 0° and 50 ml of 1N HCl was added. The red-purple solution became yellow. The mixture was extracted with ether, the ether extracts were washed with 1N HCl, dried (MgSO$_4$), and concentrated. The residue was triturated with ethanol to give 0.17 g (15%) of product; mp 227°–231°.

EXAMPLE XXI 5-(Dimethylamino)-3,4-dihydro-hydrochloride-1(2H)-isoquinolinone (21:20)

A mixture of 2.5 g (15.4 mmol) of 5-amino-3,4-dihydro-1(2H)-isoquinolinone, 66 ml of 30% formalin, 185 ml of ethanol, and 0.45 g of 5% Pd-C was hydrogenated at room temperature. The mixture was filtered and concentrated. The residue was partitioned between water and ether, the ether layer was dried (MgSO$_4$) and concentrated. Chromatography (SiO$_2$, ether to ether/methanol 9:1) gave a solid which was suspended in ethanol, treated with ethanolic HCl, and filtered to provide 1.4 g (40%) of the desired product; mp 206°–208°.

EXAMPLE XXII

1-Methoxy-5-isoquinolinamine

To a solution of 1.0 g of sodium (43.4 mmol) in methanol was added 1.42 g (6.8 mmol) of 1-chloro-5-nitroisoquinoline. The mixture was heated under reflux for three hours, cooled, and concentrated. The residue was partitioned between water and methylene chloride, dried, and filtered through SiO$_2$. The filtrate was concentrated to give 1.3 g of the 1-methoxy-5-nitroisoquinoline. This material was suspended in 150 ml of methanol, 0.3 g of 5% Pd-C was added, and the mixture was hydrogenated at room temperature for 18 hours. The mixture was filtered and concentrated. The residue was crystallized from ether/hexane to give 0.32 g (27%) of the desired product; mp 53°–57°.

EXAMPLE XXIII

4-Bromo-1-isoquinolinol

To a suspension of 5.0 g (34.5 mmol) of 1-hydroxyisoquinoline in 100 ml of methylene chloride was added 6.0 g (37.7 mmol) of bromine in 20 ml of methylene chloride. The mixture was stirred for four hours, the solid was filtered and washed with methylene chloride. This solid was recrystallized from ethanol to give 4.9 g (63%) of the desired product; mp 245°–250° (dec).

EXAMPLE XXIV

4-Bromo-5-methyl-1(2H)-isoquinolinone

To a suspension of 0.8 g (5.0 mmol) of 5-methyl-1-isoquinolinone in 30 ml of methylene chloride was added 0.85 (5.3 mmol) of bromine. The resulting orange mixture was stirred at 25° for 18 hours and diluted with 50 ml of ether. The solid was filtered and washed with methanol to give 0.35 g (29%) of product; mp 201°–210°.

EXAMPLE XXV

4-Amino-1(2H)-isoquinolinone monohydrochloride

A suspension of 2.0 g (8.92 mmol) of 4-bromo-1-isoquinolinol in 23 ml of concentrated ammonia hydroxide was heated in a sealed vessel for 16 hours at 120° C., then at 135° C. for one additional hour. The resulting yellow solution was diluted with 50 ml of water and then concentrated to 20 ml. The solid was collected, dissolved in methanol, treated with charcoal and filtered through celite. To this solution was added gaseous hydrochloric acid until a white precipitate appeared. The mixture was cooled and filtered to provide 0.62 g (35%) of the desired product; mp 275°–280° (dec).

EXAMPLE XXVI

4-Bromo-5-hydroxy-1(2H)-isoquinolinone

A mixture of 45.0 g (0.28 mol) of 1,5-dihydroxyisoquinoline and 200 ml of trifluoroacetic anhydride was heated at reflux for two hours. The resulting solution was evaporated and the solid was suspended in 300 ml of methylene chloride. To this was added 45.0 g (0.28 mol) of bromine over 15 minutes. The mixture was stirred for two hours at 25°, filtered and the solid was washed with methylene chloride and methanol to give 5.5 g of the 4-bromo-trifluoroacetyl derivative as indicated by NMR. The solid was dissolved in 6N sodium hydroxide, treated with charcoal and filtered through celite. The solution was adjusted to pH 7.5 with 6N hydrochloric acid and the resulting solid was filtered, washed with water and dried to give 23.1 g (35%) of the desired product; mp 215°–218° (dec).

EXAMPLE XXVII 3,4-Dihydro-5-[3-(1-piperidinyl)propoxy]-1(2H)-isoquinolinone

A mixture of 3.0 g (22.0 mmol) of 3,4-dihydro-5-hydroxy-1(2H)-isoquinolinone and 6.7 g (48.5 mmol) of potassium carbonate in 100 ml of ethanol was refluxed for one hour. Then 10.9 ml (100 mmol) of 1-bromo-3-chloropropanol was added and refluxing continued for five hours. The solution was cooled and concentrated. The residue was dissolved in chloroform, filtered and concentrated to provide 4.45 g (85%) of 5-(3-chloropropoxy)-3,4-dihydro-1(2H)-isoquinolinone; mp 131.5°–133°.

A mixture of 0.6 g (2.5 mmol) of 5-(3-chloropropoxy)-3,4-dihydro-1(2H)-isoquinolinone and 0.6 ml (10 mmol) of piperidine in 30 ml of ethanol was refluxed for 40 hours. The mixture was concentrated, dissolved in chloroform and washed with saturated sodium bicarbonate. The organic layer was dried and concentrated. The solid was recrystallized from water to provide 0.44 g (61%) of the desired product; mp 112°–114°.

The following examples were prepared by a similar procedure to that described in Example IV.

EXAMPLE XXVIII 3,4-Dihydro-5-[2-hydroxy-3-(1-pyrrolidinyl)propoxy]-1-(2H)-isoquinolinone mp 132°–133°.

EXAMPLE XXIX 3,4-Dihydro-5-[5-[2-hydroxy-3-(4-morpholinyl)propoxy]-1(2H)-isoquinolinone mp 154.5°–155.5°.

EXAMPLE XXX

5-[3-(Diethylamino-2-hydroxypropoxy]-3,4-dihydro-1(2H)-isoquinolinone mp 115°–116°.

EXAMPLE XXXI 3,4-Dihydro-5-[2-hydroxy-3-(methylamino)propoxy]-1(2H)-isoquinolinone mp 147°–148.5°.

The following examples were prepared by a similar procedure to that described in Example XXVII.

EXAMPLE XXXII 3,4-Dihydro-5-[3-methylamino)propoxy]-1(2H)-isoquinolinone hydrochloride mp 252°-252.5°.

EXAMPLE XXXIII 3,4-Dihydro-5-[2-(1-piperidinyl)ethoxy]-1(2H)-isoquinolinone mp 82°-85°.

EXAMPLE XXXIV 3,4-Dihydro-5-[4-(1-piperidinyl)butoxy]-1(2H)-isoquinolinone mp 107°-109°.

The following examples were prepared in a manner similar to that described in Example VII.

EXAMPLE XXXV

5-Ethoxy-3,4-dihydro-1(2H)-isoquinolinone mp 131.5°-132.5°.

EXAMPLE XXXVI 3,4-Dihydro-5-propoxy-1(2H)-isoquinolinone mp 101°-102°.

EXAMPLE XXXVII

5-Butoxy-3,4-dihydro-1(2H)-isoquinolinone mp 98.5°-99.5°.

EXAMPLE XXXVIII 3,4-Dihydro-5-(2-hydroxy-3-methoxypropoxy)-1(2H)-isoquinolinone A mixture of 1 g (6 mmol) of 3,4-dihydro-5-hydroxy-1(2H)-isoquinolinone and 2.1 g (15 mmol) of potassium carbonate in 50 ml of ethanol was refluxed for one hour. To this was added 0.65 ml (18 mmol) of glycidyl methyl ether and the mixture was refluxed overnight. The reaction was concentrated, the residue dissolved in chloroform, filtered and concentrated to an oil which solidified. The solid was recrystallized twice from water to give 0.66 g (44%) of the desired product; mp 119°-123°.

The following examples were prepared in a similar manner using the appropriate epoxide.

EXAMPLE XXXIX 3,4-Dihydro-5-(2-hydroxy-3-phenoxypropoxy)-1(2H)-isoquinolinone mp 143°-146°.

EXAMPLE XL 3,4-Dihydro-5-(2-hydroxy-3-phenylpropoxy)-1(2H)-isoquinolinone mp 148°-149.5°.

EXAMPLE XLI 3,4-Dihydro-5-(phenylethoxy)-1(2H)-isoquinolinone

This was prepared in a manner similar to that used in Example VII, substituting bromoethyl benzene for benzyl bromide, yield 88%; mp 149°-150°.

EXAMPLE XLII

5-Methoxy-4-methyl-1(2H)phthalazinone

To 0.37 g (1.48 mmol) of 2-acetyl-3-methoxy-N,N-diethylbenzamide* in 5 ml of water was added 5 ml of anhydrous hydrazine. This was heated at reflux for four hours, cooled and the resulting solid filtered and washed with water to provide 0.18 g (64%) of the desired product; mp 257°-260°.

* Obtained by known methods starting with 3-methoxy-N,N-diethylbenzamide.

EXAMPLE XLIII

Inhibition of Poly(ADP-ribose) synthetase

See Y. Shizuta, I. Seiji, K. Nakata, and O. Hayaishi, Poly (ADP-ribose) synthetase from calf thymus, (Meth. Enzymol. 66:159-165, 1980.)

Poly(ADP-ribose) synthetase is partially purified by the procedure of Shizuta, et al, up to and including the DNA-agarose column step. Active fractions were pooled and stored in small aliquots at -90°.

The enzyme assay is performed by placing the following in small glass tubes kept at 4°: 100 μl of buffer consisting of 0.5M Tris-HCl pH 8.0, 50 mM $MgCl_2$, and 5 mM dithiothreitol; 50 μl of 1 mM [$^3$H]nicotinamide adenine dinucleotide having a specific activity of 15 μCi/μmol; 100 μl of calf thymus DNA (0.3 mg/ml in water); 50 μl of calf thymus histone (Sigma, Type IIA, 0.5 mg/ml); 50 μl of inhibitor or inhibitor solvent; 150 μl of enzyme. The components are thoroughly mixed and warmed to 30° C. in a water bath. After 15 minutes the reaction is stopped by adding 2 ml of ice cold 15% trichloroacetic acid and the tubes are placed on ice for 15 minutes. The precipitate is collected on glass fiber filters and washed five times with ice cold 15% trichloroacetic acid. The filters were dried and radioactivity determined in a liquid scintillation counter. Table 1 contains the results expressed as an $IC_{50}$ which is calculated by the media effect method of T. Chou and P. Talalay, Adv. Enzyme Regul., 22:27 (1984).

TABLE 1

| Inhibition of Poly(ADP-Ribose)Synthetase | |
|---|---|
| Compound of Example | $IC_{50}$ (μm) |
| I | 0.14 |
| II | 0.10 |
| IV | 0.32 |
| V | 0.42 |
| VI | 2.11 |
| VII | 5.20 |
| VIII | 0.24 |
| IX | 0.41 |
| X | 2.55 |
| XI | 56.7 |
| XII | 0.16 |
| XIII | 0.97 |
| XIV | 0.58 |
| XV | 1.00 |
| XVI | 0.31 |
| XVII | 0.58 |
| XVIII | 0.74 |
| XIX | 1.55 |
| XX | 2.12 |
| XXXIII | 0.36 |
| XXXIV | 0.041 |
| XXV | 0.66 |
| XXVI | 0.061 |
| XXVII | 0.83 |
| XXVIII | 0.77 |
| XXIX | 1.5 |
| XXX | 1.0 |
| XXXI | 0.2 |

TABLE 1-continued

| Inhibition of Poly(ADP-Ribose)Synthetase | |
|---|---|
| Compound of Example | IC$_{50}$ ($\mu$m) |
| XXXII | 0.33 |
| XXXIII | 0.82 |
| XXXIV | 0.80 |
| XXXV | 2.6 |
| XXXVI | 0.11 |
| XXXVII | 6.0 |
| XXXVIII | 1.5 |
| XXXIX | 0.65 |
| XL | 0.34 |
| XLI | 0.60 |
| XLII | 0.08 |
| XLIX | 0.33 |
| L | 0.27 |

EXAMPLE XLIV

In Vitro Radiosensitizing Activity at 37°: Measurement of Shoulder Modifying Effects (Reduction in Dq)

The aim of this assay is to determine whether a compound is capable of radiosensitization by reducing the width of the shoulder region of an x-ray dose-response curve of V79 cells in vitro. The shoulder region represents the inherent repair capabilities of a given cell line.

Approximately 16 hours prior to experimentation, V79 cells are trypsinized and seeded into 60 mm glass petri dishes and allowed to attach overnight in a 37° incubator with a humidified environment of 95% air/5% CO$_2$.

To determine the hypoxic x-ray dose response, cells are rendered hypoxic four hours prior to the addition of the test compound by placing them in a 37° C. incubator within an anaerobic glove chamber (Forma). Drug solutions are also deoxygenated by bubbling the solution in a glass vial with 95% N$_2$/CO$_2$. Drug is added (0.1 ml into 2 ml media in petri dish) within the anaerobic chamber and drug treatment is at the highest non-toxic dose for one hour at 37°.

The oxic x-ray dose response is determined in a similar manner except that all manipulations are carried out in air.

At the end of the incubation period, cells are exposed to graded doses of x-rays (0–12.5 Gy, oxic; 0–20.0 Gy, hypoxic). Cytotoxicity controls (drug only, no irradiation) are included as well as oxic and hypoxic untreated controls (irradiation only, no drug).

Immediately following irradiation, cells are rinsed twice with 2 ml fresh media prior to the addition of 5 ml of fresh media. The cells are then incubated at 37° C. After six days, dishes are stained with crystal violet and colonies of 50 or more cells are counted to determine percent surviving cells versus x-ray dose.

In this assay, radiosensitizing activity is judged by the ability of the test compound to reduce the width of the low dose "shoulder" region of the x-ray survival curve. This is expressed by percent reduction in Dq where Dq is defined as the dose at the intersection of the regression line for the logarithmic portion of the survival curve with the 100% survival level. This is taken to represent the width of the shoulder region of the survival curve.

Table 2 summarizes the results obtained for some of the compounds. Typically, the reductions in Dq range from 18–56%. The standard 3-aminobenzamide does not reduce Dq in this assay. Also, none of the test agents had an effect on oxic cells in this assay.

EXAMPLE XLV

Inhibition of the Repair of Radiation-Induced DNA Damage as Assessed by Alkaline Elution The basic alkaline elution assay is carried out according to the procedure of K. W. Kohn, R. A. Ewig, L. C. Erickson, and L. A. Zwelling in *DNA Repair: A Laboratory Manual of Research Procedures* (eds. E. C. Freidburg and P. C. Hanawalt) with slight modifications. Briefly, suspension cultures of exponentially growing L1210 cells (total of 4×10$^6$ cells) are labeled with 0.02 $\mu$Ci/ml of [$^{14}$C] thymidine plus 1 nmol/ml of unlabeled thymidine for 24 hours prior to use. L1210 cells used as an internal standard are grown in media supplemented with 0.1 $\mu$Ci/ml of [$^3$H]thymidine and 1 nmol/ml unlabeled thymidine. For the elution protocol cells are removed from the culture flasks, centrifuged, and resuspended in fresh media. Drug treatment for experimental cells is for one hour at 37°. After the treatment period control and drug-treated cells are given a dose of 10 Gy of x-rays and incubated at 37° C. for 10 minutes to allow for repair. Samples consisting of 5×10$^5$ cells contained in 5 ml of ice cold PBS are deposited directly on 25 mm polycarbonate filters (2 micron pore size). The cells are washed with 5 ml of cold PBS, then lysed by the addition of 5 ml of lysis solution (0.2% SDS, 0.25M tetrasodium EDTA pH 9.7). All procedures commencing at the time of lysis are carried out in the dark. Subsequent to lysis samples are treated with 2 ml of lysis solution containing proteinase-K (0.5 mg/ml) for one hour. The filters are then eluted with tetrapropyl ammonium hydroxide/0.025M EDTA (free acid form)/0.1% SDS, pH 12.1, at a constant flow rate of 0.037 ml/min. Fractions of 2 ml are collected in scintillation vials. After the elution, the DNA on the filters is hydrolyzed by heating at 60° for one hour in 0.4 ml 1N HCl followed by the addition of 1 ml 1N NaOH at room temperature for one hour. To each fraction collected and the filter solution 15 ml of modified Ready-Gel scintillation fluid containing 0.7% acetic acid is added. The frequency of single-stranded DNA breakage was calculated as described by Kohn, et al. The data is corrected for the number of single-strand breaks in the central samples (~20%).

EXAMPLE XLVI

In Vivo Assay for Radiosensitization Activity

For this assay KHT fibrosarcoma tumors in hybrid mice (B6C3F$_1$) weighing 20–25 g are used. The mice are randomized and implanted SC with the appropriate tumor brei on Day 0 (one implant/mouse). Samples from each donor tumor and/or from the final brei are incubated in thioglycolate media as a check for gross bacterial contamination. On Day 8 tumors are measured in two dimensions with calipers and animals with tumor masses in the range of 500 to 700 mg are selected for the assay. At this point the tumors contain approximately 20% hypoxic cells.

The test agents are dissolved in any of several vehicles at a fixed injection dose equal to 90–100% of the maximum tolerated dose. Additional suitable controls of test compound (no irradiation) and vehicle-injected and irradiated mice are also included. Mice are irradiated at a dose of 1700 RADs at various intervals both prior to and after intraperitoneal administration of the test agents.

By using these intervals, an indication of both the optimum time to irradiate and the degree of sensitization are obtained. Irradiation of the KHT tumors is by whole body irradiation of animals in movement restricting jigs at different total exposures as indicated. The x-ray source is a Phillips 320 KV instrument with a half-value thickness of 2.0 mm copper and a target to source distance of 17 inches, with a delivery rate of 2.0 Gy/minute. Animals are monitored for signs of acute toxicity after treatment.

Radiosensitization activity is judged by survival rate of dissected and cultured cells as follows: the tumor-bearing mice are sacrificed 24 hours after treatment and the tumors aseptically removed and pooled into petri dishes. Tumors are processed for measurement of clonogenic survival, as described by D. W. Siemann, Br. J. Cancer 43:367 (1981). After incubation for 12-16 days at 37° and staining, the colonies are counted. The data are expressed as % control versus time.

EXAMPLE XLVII (R)-3,4-Dihydro-5-(2-oxiranylmethoxy)-1(2H)-isoquinolinone

A mixture of 2.0 g (12.3 mmol) of 3,4-dihydro-5-hydroxy-1(2H)-isoquinolinone, 3.3 g (14.7 mmol) of (R)-glycidal tosylate and 2.03 g (14.7 mmol) of potassium carbonate in 100 ml of ethanol were refluxed until complete (as indicated by TLC). The reaction mixture was concentrated and partitioned between ethyl acetate and water. The organic layer was dried and concentrated. The desired product, (R)-3,4-dihydro-5-(2-oxiranylmethoxy)-1(2H)-isoquinolinone, was obtained by chromatography; mp 161°-64° (Rotation= +12.5°).

EXAMPLE XLVIII (S)-3,4-Dihydro-5-(2-oxiranylmethoxy)-1(2H)-isoquinolinone

This product was obtained in a manner similar to Example XLVII; mp 161°-164° (Rotation= −11.9°).

EXAMPLE XLIX (R)-3,4-Dihydro-5-[2-hydroxy-3-(1-piperidinyl)propoxy]-1(2H)-isoquinolinone This compound was prepared in a manner similar to that used in Example IV, starting with (2R)-3,4-dihydro-5-(2-oxiranylmethoxy)-1(2H)-isoquinolinone; mp 162°-64°.

EXAMPLE L (S)-3,4-Dihydro-5-[2-hydroxy-3-(1-piperidinyl)propoxy]-1(2H)-isoquinolinone This compound was prepared in a manner similar to that used in Example IV, starting with (2S)-3,4-dihydro-5-(2-oxiranylmethoxy)-1(2H)-isoquinolinone; mp 160°-163°.

TABLE 2

| | Summary of Biological Data | | |
|---|---|---|---|
| Example | Shoulder Modification (% Reduction in DQ)* | Frequency of Unrepaired Strand Breaks** | In Vivo Radio-sensitizing Activity*** |
| I | − | + | + |
| II | + | ++ | + |
| IV | +++ | | |
| VIII | − | | |
| IX | − | +++ | |
| XII | ++ | ++++ | + |

TABLE 2-continued

| | Summary of Biological Data | | |
|---|---|---|---|
| Example | Shoulder Modification (% Reduction in DQ)* | Frequency of Unrepaired Strand Breaks** | In Vivo Radio-sensitizing Activity*** |
| XV | − | + | |

*− 1-14%
+ 15-29%
++ 30-44%
+++ ≧45%
**− 1-100
+ 101-200
++ 201-300
+++ 301-400
++++ 401-500
***+ Activity comparable to misonidazole
++ Activity greater than misonidazole More specifically, the summary of biological data for the most preferred compound in the present inventory is as follows:

Compound of Example XII $IC_{50}$ for poly(ADP-ribose)synthetase = 0.16 μm
% Reduction in Dq (37°) = 30%
Frequency of unrepaired strand breaks = 470 Rad. Eq.
Optimum time preirradiation = 2-3 hours
Enhancement Ratio (in vivo) = 1.4-1.5.

In the sensitivity assay of Example XLVI, each of the compounds of the invention tested gave a sensitizer enhancement ratio of 1.4-1.6 at a concentration which is comparable to that for misonidazole. In addition, these compounds were shown to have no unusual cytotoxicity to normal cells.

In an analogous manner, the sensitizing characteristics for chemotherapeutic agents by the methods of the present invention may be determined by an artisan. See Kato, et al noted above.

Thus, the present compounds of formula I for use as agents that enhance the lethal effects of DNA-damaging agents as described above provide an advantage of two orders of magnitude over the previously known best inhibitor of poly(ADP-ribose)synthetase 3-aminobenzamide. Since it is generally accepted that this enzyme is involved in the repair of DNA damage, it is believed inhibition of poly(ADP-ribose)synthetase or ADPRT prevents the rapid repair of radiation and chemically-induced DNA damage, resulting in enhanced cell kill of tumor cells.

Modifications of the above-described modes for carrying out the invention that are apparent to those of skill in the chemical, pharmaceutical, medical, and related arts are intended to be within the scope of the following claims.

Accordingly, the present invention is a method of radiosensitizing hypoxic tumor cells in a warm-blooded animal comprising administering a radiosensitizing effective amount of a compound of the formula I as defined above in unit dosage form.

The present invention also includes the novel compounds defined above.

Finally, the present invention also includes a pharmaceutical composition for sensitizing tumor cells to the lethal effects of DNA-damaging agents such as but not limited to ionizing radiation and/or chemotherapy agents comprising an amount of a novel compound with a pharmaceutically acceptable carrier.

We claim:

1. A compound or its pharmacologically acceptable base or acid addition salts selected from the group consisting of
   5-amino-3,4-dihydro-1(2H)isoquinolinone, and its monohydrochloride salt.
   3,4-dihydro-5-[(phenylmethyl)amino]-1(2H)-isoquinolinone;
   N-(1,2,3,4-tetrahydro-1-oxo-5-isoquinolinyl)-acetamide;
   3,4-dihydro-5-methyl-1(2H)-isoquinolinone;
   5-ethyl-3,4-dihydro-1(2H)-isoquinolinone;
   5-chloro-3,4-dihydro-1(2H)-isoquinolinone;
   3,4-dihydro-5-methoxy-1(2H)-isoquinoline-thione;
   3,4-dihydro-5-methoxy-1-(methylthio)isoquinoline;
   3,4-dihydro-3,5-dimethyl-1(2H)isoquinolinone (+/−)
   3,4-dihydro-5-methyl-1-(methylthio)isoquinoline;
   3,4-dihydro-5-(dimethylamino)-1(2H)-isoquinoline and its hydrochloride salt
   4-bromo-5-methyl-1(2H)-isoquinolinone; or
   4-bromo-5-hydroxy-1(2H)-isoquinolinone.

2. A compound or its pharmacologically acceptable base or acid addition salt selected from the group consisting of
   5-methoxy-4-methyl-1(2H)-phthalazinone;
   3,4-dihydro-5-[3-(1-piperidinyl)propoxy]-1(2H)-isoquinolinone;
   3,4-dihydro-5-[2-(1-piperidinyl)ethoxy]-(1(2H)-isoquinolinone;
   3,4-dihydro-5[4-(1-piperidinyl)butoxy]-1(2H)-isoquinolinone;
   5-ethoxy-3,4-dihydro-1(2H)-isoquinolinone;
   3,4-dihydro-5-propoxy-1(2H)-isoquinolinone;
   5-butoxy-3,4-dihydro-1(2H)-isoquinolinone;
   3,4-dihydro-5-(2-hydroxy-3-methoxypropxy)-1(2H)-isoquinolinone;
   3,4-dihydro-5-(2-hydroxy-3-phenoxypropoxy)-1(2H)-isoquinolinone;
   3,4-dihydro-5-(2-hydroxy-3-phenylpropoxy)-1(2H)-isoquinolinone; or
   3,4-dihydro-5-2-phenylethoxy-1(2H)-isoquinolinone.

3. A compound of claim 1 which is 3,4-dihydro-5-methyl-1(2H)-isoquinolinone.

4. A compound of claim 1 which is 4-bromo-5-methyl-1(2H)isoquinolinone.

5. A compound of claim 1 which is 4-bromo-5-hydroxy-1(2H)-isoquinolinone.

6. A compound of claim 2 which is 5-methoxy-4-methyl-1(2H)-phthalazinone.

7. A pharmaceutical composition for sensitizing tumor cells in a warm-blooded animal comprising a radio or chemotherapeutically potentiating effective amount of a compound of claim 1, and a pharmaceutically acceptable carrier.

8. A pharmaceutical composition for sensitizing tumor cells in a warm-blooded animal comprising a radio or chemotherapeutically potentiating effective amount of the compound of claim 2, and a pharmaceutically acceptable carrier.

* * * * *